United States Patent
Nguyen

(10) Patent No.: US 12,005,144 B2
(45) Date of Patent: Jun. 11, 2024

(54) LYOPHILIZED FORMULATIONS FOR FACTOR XA ANTIDOTE

(71) Applicant: Alexion Pharmaceuticals, Inc., Boston, MA (US)

(72) Inventor: Phuong M. Nguyen, Burlingame, CA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 17/698,718

(22) Filed: Mar. 18, 2022

(65) Prior Publication Data

US 2022/0354792 A1 Nov. 10, 2022

Related U.S. Application Data

(63) Continuation of application No. 16/078,596, filed as application No. PCT/US2017/019502 on Feb. 24, 2017, now abandoned.

(60) Provisional application No. 62/299,369, filed on Feb. 24, 2016.

(51) Int. Cl.
| | |
|---|---|
| A61K 38/00 | (2006.01) |
| A61K 9/00 | (2006.01) |
| A61K 9/19 | (2006.01) |
| A61K 38/48 | (2006.01) |
| A61K 47/18 | (2017.01) |
| A61K 47/26 | (2006.01) |
| C07K 14/00 | (2006.01) |
| C12N 9/64 | (2006.01) |

(52) U.S. Cl.
CPC .............. *A61K 9/19* (2013.01); *A61K 9/0019* (2013.01); *A61K 38/4846* (2013.01); *A61K 47/183* (2013.01); *A61K 47/26* (2013.01); *C07K 14/00* (2013.01); *C12N 9/6432* (2013.01); *C12Y 304/21006* (2013.01)

(58) Field of Classification Search
None
See application file for complete search history.

(56) References Cited

U.S. PATENT DOCUMENTS

| | | | |
|---|---|---|---|
| 5,883,077 A | 3/1999 | Brunck et al. | |
| 6,586,574 B1 | 7/2003 | Hansen et al. | |
| 8,153,590 B2 * | 4/2012 | Lu | C07K 14/435 435/325 |
| 9,056,106 B2 | 6/2015 | Sinha et al. | |
| 11,028,382 B2 * | 6/2021 | Wang | C12Y 304/21006 |
| 2004/0180827 A1 | 9/2004 | Chen et al. | |
| 2009/0098119 A1 | 4/2009 | Lu et al. | |
| 2010/0255000 A1 | 10/2010 | Sinha et al. | |
| 2011/0015128 A1 | 1/2011 | Sinha et al. | |
| 2011/0178019 A1 | 7/2011 | Rippner et al. | |
| 2012/0121580 A1 * | 5/2012 | Bhambhani | A61K 9/08 424/130.1 |
| 2013/0252979 A1 | 9/2013 | Meier et al. | |
| 2016/0237420 A1 | 8/2016 | Wang et al. | |
| 2021/0284986 A1 * | 9/2021 | Wang | A61K 9/19 |

FOREIGN PATENT DOCUMENTS

| | | |
|---|---|---|
| CA | 2362927 | 7/2011 |
| WO | WO 2000/048635 | 8/2000 |
| WO | WO 2011/017070 | 2/2011 |
| WO | WO 2011/131720 | 10/2011 |
| WO | WO 2011/088152 | 11/2011 |
| WO | WO 2013/049804 | 4/2013 |
| WO | WO 2016/029061 | 2/2016 |

OTHER PUBLICATIONS

Extended European Search Report for EP Application No. 15834421.8 dated Dec. 15, 2017, 11 pages.
Extended European Search Report for EP Application No. 17757375.5 dated Sep. 3, 2019, 8 pages.
International Search Report and Written Opinion for PCT/US2017/019502 dated May 31, 2017, 10 pages.
International Search Report for PCT/US2015/046173 dated Dec. 21, 2015, 3 pages.
Kamerzell et al. Protein Excipient Interactions: Mechanisms and Biophysical Characterization Applied to Protein Formulation Development. Advanced Drug Delivery Reviews. 2011; 63(13):1118-1159.
Padmanabhan et al. Structure of Human Des(1-45) Factor Xa at 2*2 A Resolution. Journal Mol. Biol., 1993, 232:947-966.
Registry No. 1262449-58-0 Information, Feb. 2011, 2 pages.

\* cited by examiner

*Primary Examiner* — Aradhana Sasan
*Assistant Examiner* — Mercy H Sabila
(74) *Attorney, Agent, or Firm* — Sheppard Mullin Richter & Hampton LLP

(57) ABSTRACT

The present disclosure relates to solutions and methods of preparing lyophilized formulations of factor Xa (fXa) antidotes. A suitable aqueous formulation suitable for lyophilization can include a fXa antidote, a solubilizing agent, and a stabilizer, wherein the formulation does not collapse during lyophilization.

18 Claims, No Drawings

Specification includes a Sequence Listing.

LYOPHILIZED FORMULATIONS FOR FACTOR XA ANTIDOTE

CROSS-REFERENCE TO RELATED APPLICATIONS

This application is a continuation of U.S. application Ser. No. 16/078,596, filed Aug. 21, 2018, which is a U.S. National Stage Application under 35 U.S.C. § 371 of International Application No. PCT/US2017/019502, filed Feb. 24, 2017, which claims the benefit under 35 U.S.C. § 119(e) of U.S. Provisional Application Ser. No. 62/299,369, filed Feb. 24, 2016.

SEQUENCE LISTING

The instant application contains a sequence listing which has been submitted electronically as ASCII format and is hereby incorporated by reference in its entirety. Said ASCII copy, created Mar. 16, 2022, is named 37JE225784US2_SL.txt and is 18,251 bytes in size.

BACKGROUND

Anticoagulants serve a need in the marketplace in the treatment or prevention of undesired thrombosis in patients with a tendency to form blood clots, such as, for example, those patients having clotting disorders, confined to periods of immobility or undergoing medical surgeries. One of the major limitations of anticoagulant therapy, however, is the bleeding risk associated with the treatments, and limitations on the ability to rapidly reverse the anticoagulant activity in case of overdosing or if an urgent surgical procedure is required. Thus, specific and effective antidotes to all forms of anticoagulant therapy are highly desirable.

Delivery of biologically active proteins by injection is generally the delivery route of choice when oral delivery is not practical or an immediate therapeutic activity is required. However, biological, chemical, and physical barriers such as poor long-term storage, osmolality, solubility, and stability make delivery of biologically active agents by injection to mammals problematic. Lyophilization can solve long-term storage issues. Nevertheless, there are problems that also occur with lyophilization, such as poor solubility and stability of the lyophilizate. Therefore, there exists a need for improved injectable preparations of antidotes to anticoagulants, which are stable and soluble. The disclosure satisfies these and other needs.

Any and all publications, patents, patent applications mentioned herein are hereby incorporated by reference in their entirety.

SUMMARY

The present disclosure provides lyophilized formulations of a derivative of the factor Xa (fXa) protein, referred to as the "r-Antidote" (SEQ ID NO: 8) or its variants (e.g., SEQ ID NO: 9). Compared to the wild-type fXa protein, the r-Antidote and its variants include modifications to the Gla domain and the active site, retain fXa's ability to bind to a fXa inhibitor but cannot assemble into a prothrombinase complex. The r-Antidote is a two-chain polypeptide (see SEQ ID NO. 7 in Table 3, which includes a light chain (SEQ ID NO. 2) and a heavy chain (SEQ ID NO. 3) connected with a single disulfide bond between Cysteine 98 (Cys98) of the light chain and Cysteine 108 (Cys108) of the heavy chain.

Also like the wild-type fXa, the r-Antidote undergoes post-translational modifications resulting in glycosylation at certain amino acid residues, e.g., Ser56, Ser72, Ser76 and Thr82 of the light chain and Thr249 of the heavy chain, and a modified residue, (3R)-3-hydroxyAsp at Asp29 of the light chain. Further, in addition to the inter-chain disulfide bond, there are intra-chain disulfide bonds formed between Cysteines 16 and 27, 21 and 36, 38 and 47, 55 and 66, 62 and 75, and 77 and 90 of the light chain, and between Cysteines 7 and 12, 27 and 43, 156 and 170, and 181 and 209 of the heavy chain.

Proteins such as r-Antidote can aggregate and form particles at hydrophobic interfaces when formulated into compositions suitable for administration. Therefore, during freezing and lyophilization processes, it may be desired to maintain proteins in an amorphous phase with various cryoprotectants and lyoprotectants. It also is desirable to develop a suitable amorphous formulation for high concentrations of the proteins.

Accordingly, provided herein are lyophilized compositions of proteins such as r-Antidote. Also provided herein are aqueous formulations of proteins such as r-Antidote suitable for lyophilization. In some embodiments, the lyophilized compositions are obtainable by lyophilizing an aqueous formulation as described herein.

Some embodiments provide a lyophilized composition obtainable by lyophilizing an aqueous formulation, wherein the aqueous formulation comprises a stabilizer, from 25 mM to 110 mM arginine, and at least 15 mg/mL of a two-chain polypeptide comprising a first chain comprising the amino acid sequence of SEQ ID NO. 4, and a second chain comprising the amino acid sequence of SEQ ID NO. 5, wherein the polypeptide cannot assemble into a prothrombinase complex; the aqueous formulation has a pH from 7.5 to 8; the stabilizer comprises from 2% to 7% sucrose (w/v) and from 0% to 5% mannitol (w/v); and the molar ratio of stabilizer to the polypeptide is at least 100.

In some embodiments, a lyophilized composition is obtainable by lyophilizing an aqueous formulation, wherein the aqueous formulation comprises about 45 mM arginine, about 6% sucrose (w/v), 0% mannitol, and about 20 mg/mL of a two-chain polypeptide comprising a first chain comprising the amino acid sequence of SEQ ID NO. 4, and a second chain comprising the amino acid sequence of SEQ ID NO. 5, wherein the polypeptide cannot assemble into a prothrombinase complex; and the aqueous formulation has a pH of about 7.8.

In some embodiments, a lyophilized composition is obtainable by lyophilizing an aqueous formulation, wherein the aqueous formulation comprises about 100 mM arginine, about 6% sucrose (w/v), 0% mannitol, and about 40 mg/mL of a two-chain polypeptide comprising a first chain comprising the amino acid sequence of SEQ ID NO. 4, and a second chain comprising the amino acid sequence of SEQ ID NO. 5, wherein the polypeptide cannot assemble into a prothrombinase complex; and the aqueous formulation has a pH of about 7.8.

Another embodiment of the present disclosure provides a solution prepared by dissolving the lyophilized composition of the disclosure. In some aspects, the solvent is water or saline.

Yet another embodiment provides a method of reducing bleeding in a subject undergoing anticoagulant therapy with a factor Xa inhibitor comprising administering to the subject an effective amount of a solution of the disclosure. In some aspects, the factor Xa inhibitor is apixaban, rivaroxaban or betrixaban.

DETAILED DESCRIPTION

I. Definitions

All numerical designations, e.g., pH, temperature, time, concentration, and molecular weight, including ranges, are approximations which are varied (+) or (−) by increments of 0.1 or 10%. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this disclosure. Embodiments defined by each of these transition terms are within the scope of this disclosure.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below.

"Factor Xa" or "fXa" or "fXa protein" is a serine protease in the blood coagulation pathway, which is produced from the inactive factor X (fX, SEQ ID NO. 1, Table 1). The nucleotide sequence coding human factor X ("fX") can be found in GenBank with accession number "NM_000504." Upon catalytic cleavage of the first 52 residues of the heavy chain, fX is activated to fXa. FXa contains a light chain and a heavy chain. The first 45 amino acid residues (residues 1-45 of SEQ ID NO. 1) of the light chain is called the Gla domain because it contains 11 post-translationally modified γ-carboxyglutamic acid residues (Gla). It also contains a short (6 amino acid residues) aromatic stack sequence (residues 40-45 of SEQ ID NO. 1). Chymotrypsin digestion selectively removes the 1-44 residues resulting in Gla-domainless fXa. The serine protease catalytic domain of fXa locates at the C-terminal heavy chain. The heavy chain of fXa is highly homologous to other serine proteases such as thrombin, trypsin, and activated protein C.

"Native fXa" or "wild-type fXa" refers to the fXa naturally present in plasma or being isolated in its original, unmodified form, which processes the biological activity of activating prothrombin therefore promoting formation of blood clot. The term includes naturally occurring polypeptides isolated from tissue samples as well as recombinantly produced fXa. "Active fXa" refers to fXa having the procoagulant activity of activating prothrombin. "Active fXa" may be a native fXa or modified fXa that retains procoagulant activity.

As used herein, "fXa derivatives" refer to modified fXa proteins that do not compete with fXa in assembling into the prothrombinase complex and have reduced or no procoagulant or catalytic activities, and yet bind and/or substantially neutralize the anticoagulants, such as fXa inhibitors. "Procoagulant activity" of an fXa protein or fXa derivative, in some aspects, refers to the enzymatic activity that the wild-type active fXa polypeptide carries. Examples of fXa derivatives and methods of making these derivatives are provided in U.S. Pat. Nos. 8,153,590, 8,455,441, 9,062,298, 8,268,783, and 9,109,046, U.S. Patent Publication No. 2015/0376592, and PCT publications WO2009/042962 and WO2010/056765, and further provided herein, such as SEQ ID NO: 7-9 and biological equivalents thereof.

The "enzymatic activity" of an fXa polypeptide or derivatives thereof refers to the polypeptide's ability to catalyze a biochemical reaction with a substrate through direct interaction with the substrate.

SEQ ID NO: 7 contains 3 mutations relative to the wild type fXa. The first mutation is the deletion of 6-39 aa in the Gla-domain of fX. The second mutation is replacing the activation peptide sequence 143-194 aa with -RKR-. This produces a -RKRRKR- (SEQ ID NO: 6) linker connecting the light chain (SEQ ID NO: 2) and the heavy chain (SEQ ID NO: 3). Upon secretion, this linker is cleaved resulting in a two-chain polypeptide, SEQ ID NO: 8 (r-Antidote). The third mutation is mutation of active site residue S379 to an Ala residue. This amino acid substitution is bolded in SEQ ID NO: 7-9 in Tables 2-4.

The term "r-Antidote" refers to a processed two-chain polypeptide processing product of SEQ ID NO: 7, after cleavage of the linker. This is represented by SEQ ID NO: 8. The r-antidote is disclosed in, e.g., U.S. Pat. No. 8,153,590, the content of which is incorporated to the present disclosure by reference. The r-Antidote includes a light chain (SEQ ID NO. 2) and a heavy chain (SEQ ID NO. 3) connected with a single disulfide bond between Cysteine 98 (Cys98) of the light chain and Cysteine 108 (Cys108) of the heavy chain. Like the wild-type fXa, in certain production batches, the r-Antidote undergoes post-translational modifications resulting in glycosylation at certain amino acid residues, e.g., Ser56, Ser72, Ser76 and Thr82 of the light chain and Thr249 of the heavy chain, and a modified residue, (3R)-3-hydroxyAsp at Asp29 of the light chain. Further, in addition to the inter-chain disulfide bond, there can be intra-chain disulfide bonds formed between Cysteines 16 and 27, 21 and 36, 38 and 47, 55 and 66, 62 and 75, and 77 and 90 of the light chain, and between Cysteines 7 and 12, 27 and 43, 156 and 170, and 181 and 209 of the heavy chain.

Certain variants of the r-Antidote, such as those disclosed in U.S. Pat. Nos. 8,153,590, 8,455,441, 9,062,298, 8,268,783, and 9,109,046, have similar chemical properties and biological activities as the r-Antidote. For instance, SEQ ID NO: 9 (Table 4) shows a two-chain variant that includes amino acids 129-139 of SEQ ID NO: 1 (i.e., with deletions of the Gla domain (1-45), the EGF1 domain (46-84), and the EGF2 domain (85-128)) and amino acids 429-448 of SEQ ID NO: 1 (i.e., with deletion of the beta-peptide), which is shorter than the r-Antidote but retains its antidote activities.

TABLE 1

Polypeptide Sequence of Inactive Human Factor X (SEQ ID NO: 1)

```
  1 ANSFLEEMKK GHLERECMEE TCSYEEAREV
    FEDSDKTNEF WNKYKDGDQC ETSPCQNQGK
 61 CKDGLGEYTC TCLEGFEGKN CELFTRKLCS
    LDNGDCDQFC HEEQNSVVCS CARGYTLADN
121 GKACIPTGPY PCGKQTLERR KRSVAQATSS
    SGEAPDSITW KPYDAADLDP TENPFDLLDF
```

TABLE 1-continued

Polypeptide Sequence of Inactive Human Factor X (SEQ ID NO: 1)

```
181 NQTQPERGDN NLTRIVGGQE CKDGECPWQA
    LLINEENEGF CGGTILSEFY ILTAAHCLYQ
241 AKRFKVRVGD RNTEQEEGGE AVHEVEVVIK
    HNRFTKETYD FDIAVLRLKT PITFRMNVAP
301 ACLPERDWAE STLMTQKTGI VSGFGRTHEK
    GRQSTRLKML EVPYVDRNSC KLSSSFIITQ
361 NMFCAGYDTK QEDACQGDSG GPHVTRFKDT
    YFVTGIVSWG EGCARKGKYG IYTKVTAFLK
421 WIDRSMKTRG LPKAKSHAPE VITSSPLK
```

TABLE 2

Polypeptide Sequence of the r-Antidote prior to removal of the -RKRRKR- (SEQ ID NO. 6) linker (SEQ ID NO: 7)

```
Light Chain (SEQ ID NO: 2)
  1 ANSFL                        F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER Linker (SEQ ID NO: 6)
    RKRRKR Heavy Chain (SEQ ID NO: 3)
181             IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

TABLE 3

Polypeptide Sequence of a Human Factor Xa triple mutant after removal of the -RKRRKR- (SEQ ID NO. 6) linker (SEQ ID NO: 8)

```
Light Chain (SEQ ID NO: 2)
  1 ANSFL                        F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER Heavy Chain (SEQ ID NO: 3)
181             IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

TABLE 4

Example Variant of the r-Antidote (SEQ ID NO: 9)

```
Light Chain (SEQ ID NO: 4)
121         PY PCGKQTLER

Heavy Chain (SEQ ID NO: 5)
181             IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKT
```

The present disclosure also provides a variety of biological equivalents of r-Antidote (or their precursors, represented by SEQ ID NO: 7), or alternatively polypeptides having certain sequence identity to SEQ ID NO: 8 or 9. In one aspect, such biological equivalents retain the structural characteristics of SEQ ID NO: 8 or 9, that is, a modified active site and a deleted or modified Gla domain, optionally with deletion or modification of the EGF1 and/or EGF2 domains. In another aspect, such biological equivalents retain the functional features of SEQ ID NO: 8 or 9, that is, not competing with fXa in assembling into the prothrombinase complex and having reduced or no procoagulant (e.g., enzymatic or catalytic) activities.

The term "active site" refers to the part of an enzyme or antibody where a chemical reaction occurs. A "modified active site" is an active site that has been modified structurally to provide the active site with increased or decreased chemical reactivity or specificity. Examples of active sites include, but are not limited to, the catalytic domain of human factor X comprising the 235-488 amino acid residues, and the catalytic domain of human factor Xa comprising the 195-448 amino acid residues. Examples of modified active site include, but are not limited to, the catalytic domain of human factor Xa comprising 195-448 amino acid residues in SEQ ID NO: 1 with at least one amino acid substitution at position Arg306, Glu310, Arg347, Lys351, Lys414, or Arg424.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

The term "lyophilized formulation" refers to a pharmaceutical formulation or composition comprising a polypeptide of interest that is freeze-dried.

The term "substantially amorphous" material embraces material which has no more than about 10% crystallinity; and "amorphous" material embraces material which has no more than about 2% crystallinity.

As used herein, the term "bulking agent" refers to an ingredient that provides bulk to the lyophilized formulation. Examples of bulking agents include, without limitation, mannitol, trehalose, lactose, sucrose, polyvinyl pyrrolidone, sucrose, glucose, glycine, cyclodextrins, dextran, solid PEGs and derivatives and mixtures thereof. In one embodiment, a formulation of the present disclosure optionally includes a bulking agent.

As used herein, the term "lyophilization" or freeze drying refers to a process in which water is removed from a product after it is frozen and placed under a vacuum, allowing the ice to change directly from solid to vapor without passing through a liquid phase. The process consists of three separate, unique, and interdependent processes; freezing, primary drying (sublimation), and secondary drying (desorption). Methods for lyophilizing polypeptides used in this disclosure are described herein and well known in the art.

The term "stabilizer" denotes a pharmaceutical acceptable excipient, which protects the active ingredient (e.g., the fXa derivative polypeptides) and/or the formulation from chemical and/or physical degradation during manufacturing, storage and application. The stabilizer may be a cryoprotectant or lyoprotectant. Examples of stabilizers may be include sucrose, arginine, citrate, mannitol, trehalose, glycine, sodium chloride, dextran and glucose. In some embodiments, the stabilizer is amorphous.

"Cryoprotectants" are known in the art and include without limitation, e.g., sucrose, trehalose, and glycerol. A cryoprotectant exhibiting low toxicity in biological systems is generally used.

A "lyoprotectant" refers to a pharmaceutically acceptable substance that stabilizes a protein during lyophilization (the process of rapid freezing and drying in a high vacuum). Examples of lyoprotectants include, without limitation, sucrose, or trehalose.

As used herein, the term "surfactant" refers to a pharmaceutically acceptable organic substance having amphipathic structures; namely, it is composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants may lower the surface tension (or interfacial tension) between two liquids or between a liquid and a solid. Such surfactants, e.g., minimize aggregation of lyophilized particles during reconstitution of the product. Surfactants are often used as wetting, emulsifying, solubilizing, and dispersing agents for various pharmaceutical compositions and preparations of biological materials. In some embodiments of the pharmaceutical formulations described herein, the amount of surfactant is described as a percentage expressed in weight/volume percent (w/v %). Suitable pharmaceutically acceptable surfactants include but are not limited to the group of fatty acid and alkyl sulfonates, benzethanium chloride (e.g., HY AMINE 1622); polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), or sodium dodecyl sulphate (SDS). Polyoxyethylenesorbitan-fatty acid esters include polysorbate 20, (sold under the trademark Tween20™) and polysorbate 80 (sold under the trademark Tween 80™). Polyethylene-polypropylene copolymers include those sold under the names Pluronic® F68 or Poloxamer188™. Polyoxyethylene alkyl ethers include those sold under the trademark Brij™ Alkylphenolpolyoxyethylene ethers include those sold under the tradename Triton-X. Natural surfactants may also be used, such as sodium taurocholic acid, 1-palmitoyl-2-Sn-glycero-3-phosphocholine, lecithin and other phospholipids. Surfactants may comprise from about 0.001% to about 5% w/v.

A "crystalline component" refers to a molecule that forms a crystalline matrix in a formulation that includes a polypeptide, during a freeze drying process. Non-limiting examples of crystalline components include mannitol and glycine.

The term "solubilizing agent" refers to salts, ions, carbohydrates, complexation agent, polymers and other compounds which, when present in solution, increases the solubility of another molecule (e.g., an active ingredient) in the solution. Non-limiting examples of solubilizing agents include arginine and citrate. In one aspect, the solubilizing agent is arginine. In one aspect, the solubilizing agent is citrate.

The term "buffer" as used herein denotes a pharmaceutically acceptable excipient, which stabilizes the pH of a pharmaceutical preparation. Suitable buffers are well known in the art and can be found in the literature. Pharmaceutically acceptable buffers comprise but are not limited to tris-buffers, arginine-buffers, histidine-buffers, citrate-buffers, succinate-buffers and phosphate-buffers. Independently from the buffer used, the pH can be adjusted with an acid or a base known in the art, e.g., succinic acid, hydrochloric acid, acetic acid, phosphoric acid, sulfuric acid and citric acid, succinate, citrate, tris base, histidine, histidine HCl, sodium hydroxide and potassium hydroxide. Suitable buffers include, without limitation, histidine buffer, 2-morpholinoethanesulfonic acid (MES), cacodylate, phosphate, acetate, succinate, and citrate. The concentration of the buffer can be between about 4 mM and about 60 mM, or alternatively about 4 mM to about 40 mM, or alternatively about 5 mM to about 25 mM.

An "antioxidant" refers to a molecule capable of slowing or preventing the oxidation of other molecules. Oxidation is a chemical reaction that transfers electrons from a substance to an oxidizing agent. Oxidation reactions can produce free radicals, which start chain reactions that destabilize the protein therapeutics and ultimately affect the product activity. Antioxidants terminate these chain reactions by removing free radical intermediates, and inhibit other oxidation reactions by being oxidized themselves. As a result, antioxidants are often reducing agents, chelating agent and oxygen scavengers such as citrate, EDTA, DPTA, thiols, ascorbic acid or polyphenols. Non-limiting examples of antioxidants include ascorbic acid (AA, E300), thiosulfate, methionine, tocopherols (E306), propyl gallate (PG, E310), tertiary butylhydroquinone (TBHQ), butylated hydroxyanisole (BHA, E320) and butylated hydroxytoluene (BHT, E321).

A "preservative" is a natural or synthetic chemical that is added to products such as foods, pharmaceuticals, paints, biological samples, wood, etc. to prevent decomposition by microbial growth or by undesirable chemical changes. Preservative additives can be used alone or in conjunction with other methods of preservation. Preservatives may be antimicrobial preservatives, which inhibit the growth of bacteria and fungi, or antioxidants such as oxygen absorbers, which inhibit the oxidation of constituents. Common antimicrobial preservatives include, benzalkonium chloride, benzoic acid, cholorohexidine, glycerin, phenol, potassium sorbate, thimerosal, sulfites (sulfur dioxide, sodium bisulfite, potassium hydrogen sulfite, etc.) and disodium EDTA. Other preservatives include those commonly used in patenteral proteins such as benzyl alcohol, phenol, m-cresol, chlorobutanol or methylparaben.

The term "tonicity agent" as used herein denotes pharmaceutically acceptable agents used to modulate the tonicity of the formulation. Isotonicity generally relates to the osmotic pressure relative to a solution, usually relative to that of human blood serum. A formulation can be hypotonic, isotonic or hypertonic. In one aspect, the formulation is isotonic. An isotonic formulation is liquid or liquid reconstituted from a solid form, e.g. from a lyophilized form and denotes a solution having the same tonicity as some other solution with which it is compared, such as physiologic salt solution and the blood serum. Suitable isotonicity agents include but are not limited to sodium chloride, potassium chloride, glycerin and any component from the group of amino acids, sugars, as defined herein as well as combinations thereof.

II. Formulations

As provided, the wild-type fXa is a two-chain polypeptide. So are many forms of fXa antidotes, including the r-Antidote (SEQ ID NO: 8 and 9), which includes a light chain (SEQ ID NO. 2 or 4) and a heavy chain (SEQ ID NO. 3 or 5) connected with a single disulfide bond between Cysteine 98 (Cys98 in SEQ ID NO: 2, or Cys4 in SEQ ID NO: 4): of the light chain and Cysteine 108 (Cys108 in SEQ ID NO: 3 or 5) of the heavy chain. Also like the wild-type fXa, the r-Antidote expressed in cells undergoes post-translational modifications resulting in glycosylation at certain amino acid residues, e.g., Ser56, Ser72, Ser76 and Thr82 of the light chain and Thr249 of the heavy chain, and a modified residue, (3R)-3-hydroxyAsp at Asp29 of the light chain. Further, in addition to the inter-chain disulfide bond, there can be one or more intra-chain disulfide bonds formed between Cysteines 16 and 27, 21 and 36, 38 and 47, 55 and 66, 62 and 75, and 77 and 90 of the light chain, and between Cysteines 7 and 12, 27 and 43, 156 and 170, and 181 and 209 of the heavy chain.

Given the two-chain structure and various post-translational modifications of the fXa antidotes, development of a stable lyophilized formulation that includes a high concentration of the polypeptide is a great challenge.

It is desirable to develop a suitable amorphous formulation for high concentrations of the polypeptide. With higher concentrations of polypeptide, higher concentrations of amorphous stabilizer (i.e., cryoprotectants and lyoprotectants) may be needed, while still maintaining an appropriate osmolality for delivery. In mixed systems of amorphous and crystalline components, higher amounts of the amorphous stabilizer (i.e. cryoprotectants and lyoprotectants) can increase the glass transition temperature (Tg') while a crystalline component decreases Tg' in formulations comprising high concentrations of a polypeptide. As such, higher concentrations of a stabilizer and lower concentrations of a crystalline component can increase Tg'. Formulations with high Tg' are desirable as these formulations can be more amenable for lyophilization, if needed.

Accordingly, it was found that, when mannitol and sucrose are present in formulations of the present disclosure, formulations with a ratio of sucrose to mannitol greater than 1 were amorphous and exhibited a Tg'. It was also found that lyophilized, amorphous formulations may be achieved when a crystalline component is not present and an amorphous stabilizer is included in the formulation. It is also contemplated that increasing concentrations of the stabilizer (such as a lyoprotecting agent) can increase the stability of the polypeptide.

It was also found that increasing concentrations of a polypeptide as described herein can increase the Tg'. High concentrations of a polypeptide can be achieved at higher pH or by increasing the addition of a solubilizing agent, such as arginine.

More specifically, a suitable lyophilized, amorphous formulation can be generated from aqueous formulations as described herein. An exemplary r-Antidote solution includes about 100 mM arginine (90 mM to about 110 mM), about 6% sucrose (4-5%), and 0% mannitol (i.e. does not include mannitol). Another exemplary r-Antidote solution includes about 45 mM arginine (35 mM to about 55 mM), about 6% sucrose (4-5%), and 0% mannitol (i.e. does not include mannitol). Further, these solutions include about 10 mM tris (about 5 mM to about 15 mM), and 0.01%-0.02% (0.001%-0.5%) polysorbate 80 (PS80) along with a desired amount of r-Antidote (e.g., 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 110 mg/mL, 115 mg/mL, 120 mg/mL, 125 mg/mL, 130 mg/mL, 135 mg/mL, 140 mg/mL, 145 mg/mL, or 150 mg/mL), and has a pH of about 7.8.

Accordingly, when these solutions are lyophilized, it will form a composition that maintains the stabilizer (such as sucrose) and/or polypeptide in an amorphous form. In some embodiments, formulations described herein exhibit a glass transition temperature from about −5° C. to about −50° C., −10° C. to about −45° C., −15° C. to about −40° C., −20° C. to about −30° C., or about −27° C. to about −37° C.

The results observed with the r-Antidote can be readily extrapolated to other fXa antidotes that have similar structures including biological equivalents of r-Antidote (or their precursors, represented by SEQ ID NO: 2). In one aspect, such biological equivalents have at least 80%, 85%, 90%, or 95% sequence identity to SEQ ID NO: 8 or 9. In one aspect, such biological equivalents include two peptide chains, each having at least 80%, 85%, 90%, or 95% sequence identity to SEQ ID NO: 2 or 4 or SEQ ID NO: 3 or 5, respectively. In one aspect, such biological equivalents retain the structural characteristics of SEQ ID NO: 8, that is, a modified active site and a deleted or modified Gla domain. In another aspect, such biological equivalents retain the functional features of SEQ ID NO: 8, that is, not competing with fXa in assembling into the prothrombinase complex and having reduced or no procoagulant (e.g., enzymatic or catalytic) activities. In one aspect, such biological equivalents retain the structural characteristics of SEQ ID NO: 9, that is, a modified active site and a deleted or modified Gla and either or both EGF1 and EGF2 domains. In another aspect, such biological equivalents retain the functional features of SEQ ID NO: 9, that is, not competing with fXa in assembling into the prothrombinase complex and having reduced or no procoagulant (e.g., enzymatic or catalytic) activities.

Also, it is contemplated that arginine can be substituted with another solubilizing agent and sucrose can be substituted with another stabilizer (i.e., cryoprotectant or lyoprotectant), adequate examples of each of which are available in the art and are provided in the present disclosure.

A. Polypeptide Solution Suitable for Lyophilization

In one embodiment, the present disclosure provides an aqueous formulation suitable for lyophilization, which formulation includes a fXa antidote as disclosed here or its biological equivalents, along with a solubilizing agent and a stabilizer (i.e. cryoprotectant or lyoprotectant), wherein the molar ratio of the stabilizer to fXa antidote is about 100 or higher. The aqueous formulation can further include a surfactant and/or a buffer. In some aspects, the presence of each of these agents maintains the fXa antidote in an amorphous form. In some aspects, the presence of each of these agents prevents the fXa antidote from collapsing during lyophilization, for instance, when the freeze-dry temperature is higher than −30° C., −25° C., −20° C., −15° C., −10° C., −5° C., or 0° C.

One embodiment of the disclosure provides an aqueous formulation which can be used for lyophilization. The aqueous formulation includes a fXa derivative polypeptide, e.g., a polypeptide comprising the amino acid sequence of SEQ ID NO. 8 or 9 or an amino acid sequence having at least 95% sequence identity to SEQ ID NO. 8 or 9. In addition to the polypeptide, the aqueous formulation further includes a solubilizing agent and a stabilizer, wherein the molar ratio of the stabilizer to fXa derivative polypeptide is about 100 or higher.

In one aspect, the fXa derivative polypeptide has modifications to the Gla domain and the active site as compared to the wild-type fXa protein. In one aspect, the fXa derivative polypeptide retains fXa's ability to bind to a fXa inhibitor but does not assemble into a prothrombinase complex. In one aspect, the fXa derivative polypeptide is a two-chain polypeptide having an amino acid sequence of SEQ ID NO. 8, which includes a light chain (SEQ ID NO. 2) and a heavy chain (SEQ ID NO. 3) connected with a single disulfide bond between Cysteine 98 (Cys98) of the light chain and Cysteine 108 (Cys108) of the heavy chain. In one aspect, the fXa derivative polypeptide is a two-chain polypeptide having an amino acid sequence of SEQ ID NO. 9, which includes a light chain (SEQ ID NO. 4) and a heavy chain (SEQ ID NO. 5) connected with a single disulfide bond between Cysteine 4 (Cys4) of the light chain and Cysteine 108 (Cys108) of the heavy chain. In one aspect, the aqueous formulation includes at least 15 mg/mL of the polypeptide. In one aspect, the aqueous formulation includes at least 5, 10, 15, 20, 25, 30, 35, 40, 45, 50, 55, 60, 65, 70, 75, 80, 85, 90, 95, 100, 105, 110, 115, 120, 125, 130, 135, 140, 145, or 150 mg/mL of the polypeptide.

In some aspects, a solubilizing agent is included in the aqueous formulation. The presence of the solubilizing agent is demonstrated herein to be useful in keeping the fXa polypeptide soluble and stable in the formulation. In some aspects, the concentration of the solubilizing agent (e.g., arginine) is at least 40 mM, or alternatively at least 20 mM, 25 mM, 30 mM, 35 mM, 45 mM, 50 mM, 60 mM, 70 mM, 80 mM, 90 mM, or 100 mM. In some aspects, the concentration of the solubilizing agent (e.g., arginine) is not higher than 150 mM, 145 mM, 140 mM, 135 mM, 130 mM, 125 mM, 120 mM, 115 mM, or 110 mM. In some aspects, the concentration of the solubilizing agent is from about 25 mM to about 110 mM, about 20 mM to about 130 mM, about 30 mM to about 120 mM, or about 40 mM to about 110 mM, or about 40 mM to about 105 mM. In some aspects, the concentration of the solubilizing agent is about 40 mM to about 50 mM or about 45 mM. In some aspects, the concentration of the solubilizing agent is about 90 mM to about 110 mM, or about 95 mM to about 105 mM, or about 100 mM. It is noted that as used herein, the term arginine refers to the amino acid as well as the salts (e.g., arginine HCl) thereof. Arginine has a molecular weight of about 174.2 Dalton and arginine HCl (e.g., L-arginine HCl) has a molecular weight of about 210.7 Dalton.

In one embodiment, the solubilizing agent is citrate or a salt thereof. The salt of citrate is sodium citrate. In one aspect, the citrate comprises a concentration from about 1.0 mM to about 200.0 mM. In a further aspect, the concentration of the citrate is about 25 mM. In another aspect, the concentration of the citrate is about 50 mM. In further embodiment, the concentration of the citrate is about 5 mM, 10 mM, or 20 mM. In another embodiment, the citrate comprises a concentration from about 0.05 M to about 0.2 M.

In some aspects, a stabilizer is included in the aqueous formulation. In one aspect, the stabilizer is amorphous mannitol and/or amorphous sucrose. In one aspect, the stabilizer is amorphous sucrose.

In one aspect, the concentration of the stabilizer in the aqueous formulation (e.g., sucrose) is at least about 1.5% (w/v). In one aspect, the concentration of the stabilizer in the aqueous formulation (e.g., sucrose) is at least about 2.5%, 3%, 3.5%, 4%, 4.5%, 5%, 5.5%, 6%, 6.5%, or about 7% (w/v). In one aspect, the concentration of the stabilizer in the aqueous formulation (e.g., sucrose) is not greater than about 10%, 9.5%, 9%, 8.5%, 8%, 7.5%, or 7% (w/v). In one aspect, the concentration of the stabilizer in the aqueous formulation (e.g., sucrose) is from about 2% to about 8%, or from about 2% to about 7%, or from about 2.5% to about 7.5%, or from about 3% to about 7%, or from about 3.5% to about 6.5%, or from about 4% to about 7%, or from about 4% to about 6%, or from about 4.5% to about 5.5%, or from about 3% to about 5%, or from about 3.5% to about 4.5%, or from 5% to 7%, or from about 5.5% to about 7.5%, or from about 5.5% to about 6.5%, or at about 3.5%, 4%, 4.5%, 5%, 5.5%, 6%, 6.5%, or 7% (w/v).

In one aspect, the concentration of mannitol in the aqueous formulation is from about 0% to about 5% (w/v), about 0% to about 4%, or about 0% to about 3%. In some embodiments, the concentration of mannitol in the aqueous formulation is at least about 0.001%, about 0.5%, about 1%, about 1.5%, or about 2% (w/v). In one aspect, the concentration of the mannitol in the aqueous formulation is not greater than about 6%, about 5.5%, about 5%, about 4.5%, about 4%, or about 3.5% (w/v). In some embodiments, the aqueous formulation does not include mannitol.

In one aspect, the molar ratio of the stabilizer to protein in the aqueous formulation is at least about 50, at least about 75, at least about 100, at least about 200, at least about 300, at least about 400, at least about 500, at least about 600, at least about 700, at least about 800, at least about 900, or at least about 1000. In one aspect, the molar ratio of the stabilizer to protein in the aqueous formulation is 10 to about 1000, about 50 to about 900, about 60 to about 800, about 70 to about 700, about 80 to about 800, about 90 to about 700, about 100 to about 600, about 100 to about 500, 100 to about 400, 110 to about 380, about 150 to about 200, about 175 to about 185, about 350 to about 400, or about 355 to about 365. In some aspects, the molar ratio of the stabilizer to protein in the aqueous formulation is at least about 90, 110, 120, 130, 140, or 150.

In some aspects, the aqueous formulation can further include a surfactant, a buffer, a tonicity agent, a cryoprotectant, a surfactant, a lyoprotectant, a preservative or combinations thereof.

In some aspects, the aqueous formulation has a pH that is 6 or higher, or 6.5 or higher, or 7 or higher, or 7.5 or higher. In some aspects, the pH is not higher than 9, 8.5, or 8. In some aspects, the pH is between 6 and 9, between 6.5 and 8.5, between 7 and 8.5, between 7.5 and 8.2, between 7.6 and 8.1, between 7.7 and 7.9, or at about 6.7, 6.8, 6.9, 7, 7.1, 7.2, 7.3, 7.4, 7.5, 7.6, 7.7, 7.8, 7.9 or 8.

In some embodiments, in addition to the polypeptide, the aqueous formulation further includes a solubilizing agent, crystalline component (such as mannitol), and a stabilizer (such as sucrose), wherein the ratio of the stabilizer to crystalline component is sufficiently high to prevent crystallization. Such formulations also do not collapse during lyophilization under desired conditions and can be lyophilized to obtain lyophilized, amorphous compositions. In one aspect, the desired condition is freeze drying at a temperature that is higher than −40° C., or alternatively higher than −30° C., −25° C., −20° C., −15° C., or −10° C. In another aspect, the desired condition is freeze drying at a temperature that is lower than 5° C., 0° C., −5° C., or −10° C.

In some aspects, the aqueous formulation can include a buffer, wherein the buffer is Tris. In such embodiments, the aqueous formulation can include at least about 1 mM tris, 2 mM tris, 4 mM tris, 6 mM tris, 8 mM tris, 10 mM tris, 12 mM tris, 14 mM tris, 16 mM tris, 18 mM tris, or 20 mM tris. In some aspects, the aqueous formulation can include less than about 35 mM tris, 33 mM tris, 30 mM tris, 28 mM tris, 26 mM tris, or 25 mM tris.

In some aspects, the aqueous formulation can include a surfactant, such as polysorbate 80. In some aspects, the concentration of the polysorbate 80 is from about 0.0001% to about 1%, 0.001% to about 0.9%, 0.001% to about 0.5%, about 0.001% to about 0.3%, about 0.005% to about 0.03%, about 0.005% to about 0.02%, or about 0.01% to about 0.02%. In some aspects, the concentration of the polysorbate 80 is at least about 0.0001%, 0.001%, or 0.002%.

In one aspect, the aqueous formulation includes about 45 mM arginine, about 6% sucrose (w/v), and about 20 mg/mL of a two-chain r-Antidote, wherein the formulation has a pH of about 7.8. In one aspect, the aqueous formulation includes about 100 mM arginine, about 6% sucrose (w/v), and about 40 mg/mL of a two-chain r-Antidote, wherein the formulation has a pH of about 7.8. In one aspect, the aqueous formulation includes about 100 mM arginine, about 6% sucrose (w/v), and about 40 mg/mL of a two-chain r-Antidote, wherein the formulation has a pH of about 7.8. In one aspect, the aqueous formulation further includes 0.005%-0.02% (w/v) Polysorbate 80 and a buffer. In one aspect, the aqueous formulation further includes 0.01% (w/v) Polysorbate 80 and a buffer.

B. Lyophilization and lyophilized compositions

Also provided, in some embodiments, are methods of lyophilizing the aqueous formulations of the present disclosure.

In another aspect, the lyophilization cycle includes the steps as described in Table 9. It is further noted that, once an aqueous solution suitable for lyophilization is identified, the method of lyophilizing the solution can be derived accordingly, with methods known in the art. In one aspect, one, or more or all of the drying steps are carried out at a temperature of −40° C. or higher. In one aspect, the drying steps are carried out at a temperature of about −35° C., −30° C., −25° C., −20° C., −15° C., −10° C., −5° C., or 0° C.

In some aspects, also provided are lyophilized, amorphous compositions prepared by lyophilizing the aqueous formulation of the present disclosure. Based on the concentrations of each agent in the aqueous formulation, the relative content of the agent in the lyophilized composition can readily be determined.

In one aspect, the lyophilized composition includes at least 5%, or alternatively at least 10%, 15%, 20%, 25%, 30%, 35%, 40%, 45%, 50%, 55% or 60% (w/w) of the fXa derivative polypeptide. In some embodiments, the lyophilized composition comprises sucrose in amorphous form.

Still, in some aspects, provided is a solution prepared by dissolving the lyophilized composition of the present disclosure in a solvent. In some aspects, the solvent is water or saline. In one aspect, the solvent is water. In one aspect, the solution includes at least 20 mg/ml or alternatively at least 40 mg/ml of the target polypeptide.

III. Methods of Using the Formulations

The present disclosure also relates to therapeutic methods of treating, preventing or reducing bleeding in a subject undergoing anticoagulant therapy with a fXa inhibitor comprising administering to a subject an effective amount of the lyophilized formulation upon being dissolved in a suitable solvent. It is contemplated that the antidotes or derivatives of the present disclosure may be short-duration drugs to be used in elective or emergency situations, which can safely and specifically neutralize a fXa inhibitor's conventional anticoagulant properties without causing deleterious hemodynamic side-effects or exacerbation of the proliferative vascular response to injury.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

"Treating" also covers any treatment of a disorder in a mammal, and includes: (a) preventing a disorder from occurring in a subject that may be predisposed to a disorder, but may have not yet been diagnosed as having it, e.g., prevent bleeding in a patient with anticoagulant overdose; (b) inhibiting a disorder, i.e., arresting its development, e.g., inhibiting bleeding; or (c) relieving or ameliorating the disorder, e.g., reducing bleeding.

As used herein, to "treat" further includes systemic amelioration of the symptoms associated with the pathology and/or a delay in onset of symptoms. Clinical and subclinical evidence of "treatment" will vary with the pathology, the individual and the treatment.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. A "subject" of diagnosis or treatment is a cell or a mammal, including a human. Non-human animals subject to diagnosis or treatment include, for example, murine, such as rats, mice, canine, such as dogs, leporids, such as rabbits, livestock, sport animals, and pets.

The agents and compositions of the present disclosure can be used in the manufacture of medicaments and for the treatment of humans and other animals by administration in accordance with conventional procedures, such as an active ingredient in pharmaceutical compositions.

An agent of the present disclosure can be administered for therapy by any suitable route, specifically by parental (including subcutaneous, intramuscular, intravenous and intradermal) administration. It will also be appreciated that the preferred route will vary with the condition and age of the recipient, and the disease being treated.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof.

"Anticoagulant agents" or "anticoagulants" are agents that inhibit blood clot formation. Examples of anticoagulant agents include, but are not limited to, specific inhibitors of thrombin, factor IXa, factor Xa, factor XIa, factor XIIa or factor VIIa, heparin and derivatives, vitamin K antagonists, and anti-tissue factor antibodies. Examples of specific inhibitors of thrombin include hirudin, bivalirudin (Angiomax®), argatroban and lepirudin (Refludan®). Examples of heparin and derivatives include unfractionated heparin (UFH), low molecular weight heparin (LMWH), such as enoxaparin (Lovenox®), dalteparin (Fragmin®), and danaparoid (Orgaran®); and synthetic pentasaccharide, such as fondaparinux (Arixtra®). Examples of vitamin K antagonists include warfarin (Coumadin®), phenocoumarol, acenocoumarol (Sintrom®), clorindione, dicumarol, diphenadione, ethyl biscoumacetate, phenprocoumon, phenindione, and tioclomarol. In one embodiment, the anticoagulant is an inhibitor of factor Xa. In one embodiment, the anticoagulant is betrixaban.

"Anticoagulant therapy" refers to a therapeutic regime that is administered to a patient to prevent undesired blood clots or thrombosis. An anticoagulant therapy comprises administering one or a combination of two or more anticoagulant agents or other agents at a dosage and schedule suitable for treating or preventing the undesired blood clots or thrombosis in the patient.

The term "factor Xa inhibitors" or "inhibitors of factor Xa" refer to compounds that can inhibit, either directly or indirectly, the coagulation factor Xa's activity of catalyzing conversion of prothrombin to thrombin in vitro and/or in vivo.

"Direct factor Xa inhibitors" bind to the fXa directly and non-limiting examples include NAP-5, rNAPc2, tissue factor pathway inhibitor (TFPI), DX-DX-9065a (as described in, e.g., Herbert, J. M., et al, *J Pharmacol Exp Ther.* 1996 276(3):1030-8), YM-60828 (as described in, e.g., Taniuchi, Y., et al, *Thromb Haemost.* 1998 79(3):543-8), YM-150 (as described in, e.g., Eriksson, B. I. et. al, *Blood* 2005; 106 (11), Abstract 1865), apixaban, rivaroxaban, TAK-442, PD-348292 (as described in, e.g., Pipeline Insight: Antithrombotics—Reaching the Untreated Prophylaxis Market, 2007), otamixaban, edoxaban (as described in, e.g., Hylek EM, Curr Opin Invest Drugs 2007 8(9):778-783), LY517717 (as described in, e.g., Agnelli, G., et al, *J. Thromb. Haemost.* 2007 5(4):746-53), GSK913893, razaxaban, betrixaban or a pharmaceutically acceptable salt thereof, and combinations thereof. In a particular aspect, the direct factor Xa inhibitor is rivaroxaban. In some aspects, a direct fXa inhibitor is a small molecule chemical compound.

"Indirect factor Xa inhibitors" inhibition of the fXa activity is mediated by one or more other factors. Non-limiting examples of indirect factor Xa inhibitors include fondaparinux, idraparinux, biotinylated idraparinux, enoxaparin, fragmin, tinzaparin, low molecular weight heparin ("LMWH"), and combinations thereof. In a particular aspect, the indirect factor Xa inhibitor is enoxaparin.

In one embodiment, the factor Xa inhibitor is selected edoxaban, fondaparinux, idraparinux, biotinylated idraparinux, enoxaparin, fragmin, NAP-5, rNAPc2, tissue factor pathway inhibitor, DX-9065a, YM-60828, YM-150, apixaban, rivaroxaban, PD-348292, otamixaban, DU-176b, LY517717, GSK913893, razaxaban, low molecular weight heparin, betrixaban or a pharmaceutically acceptable salt thereof, and combinations thereof.

The term "betrixaban" refers to the compound "[2-({4-[(dimethylamino)iminomethyl]phenyl}carbonylamino)-5-methoxyphenyl]-N-(5-chloro(2-pyridyl))carboxamide" or pharmaceutically acceptable salts thereof. "[2-({4-[(dimethylamino)iminomethyl]phenyl}carbonylamino)-5-methoxyphenyl]-N-(5-chloro(2-pyridyl))carboxamide" refers to the compound having the following structure:

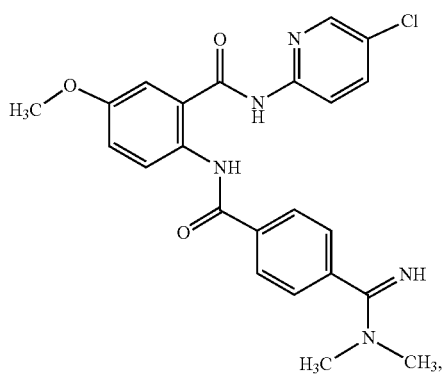 [SMILES: COc1ccc(NC(=O)c2ccc(C(=N)N(C)C)cc2)c(C(=O)Nc2ccc(Cl)cn2)c1]

or a tautomer or pharmaceutically acceptable salt thereof. In one embodiment, it is the maleate salt.

Betrixaban is described in U.S. Pat. Nos. 6,376,515 and 6,835,739 and U.S. Patent Application Publication No. 2007/0112039, filed on Nov. 7, 2006, the contents of which are incorporated herein by reference. Betrixaban is known to be a specific inhibitor of factor Xa.

"Neutralize," "reverse" or "counteract" the activity of an inhibitor of fXa or similar phrases refer to inhibit or block the factor Xa inhibitory or anticoagulant function of a fXa inhibitor. Such phrases refer to partial inhibition or blocking of the function, as well as to inhibiting or blocking most or all of fXa inhibitor activity, in vitro and/or in vivo.

"An effective amount" refers to the amount of derivative sufficient to induce a desired biological and/or therapeutic result. That result can be alleviation of the signs, symptoms, or causes of a disease, or any other desired alteration of a biological system. In the present disclosure, the result will typically involve one or more of the following: neutralization of a fXa inhibitor that has been administered to a patient, reversal of the anticoagulant activity of the fXa inhibitor, removal of the fXa inhibitor from the plasma, restoration of hemostasis, and reduction or cessation of bleeding. The effective amount will vary depending upon the specific antidote agent used, the specific fXa inhibitor the subject has been administered, the dosing regimen of the fXa inhibitor, timing of administration of the antidote, the subject and disease condition being treated, the weight and age of the subject, the severity of the disease condition, the manner of administration and the like, all of which can be determined readily by one of ordinary skill in the art.

In certain aspects, the solution is administered to deliver an amount of the fXa derivative (e.g., the r-antidote) from about 10 milligrams (mg) to about 2 grams (g). Other amounts of the r-antidote used include from about 100 mg to about 1.5 g; from about 200 mg to about 1 g; and from about 400 mg to about 900 mg. In some aspects, the amount of the r-antidote used is about 400 mg or 960 mg. In some aspects, the amount of the r-antidote used is from about 10 mg to about 100 mg; from about 15 mg to about 95 mg; and from about 20 mg to about 80 mg.

In another embodiment, the solution administered in a neutralizing amount that is at least about a 1:1 fold molar ratio of circulating concentration of r-antidote over circulating concentration of the factor Xa inhibitor for a period of at least about 30 minutes. In other embodiments the molar ratio is about 1:1 or about 2:1 or about 4:1.

The formulation when administered neutralizes the factor Xa inhibitor by at least about 20%, or by at least about 50%, or by at least about 75%, or by at least about 90%, or by at least about 95%.

One can determine if the method, i.e., inhibition or reversal of a factor Xa inhibitor is achieved, by a number of in vitro assays, such as thrombin generation assay, and clinical clotting assays such as aPTT, PT and ACT.

One aspect of the present disclosure relates methods of selectively binding and inhibiting an exogenously administered fXa inhibitor in a subject undergoing anticoagulant therapy with a fXa inhibitor comprising administering to the subject an effective amount of a solution of the lyophilized formulation. Patients suitable for this therapy have undergone prior anticoagulant therapy, for example, they have been administered one, or more of an anticoagulant, such as a direct or indirect inhibitor of fXa.

In some embodiments, the solution is administered after the administration of an overdose of a fXa inhibitor or prior to a surgery, which may expose subjects to the risk of hemorrhage. The subject may be a cell or a mammal, such as a human.

In another aspect the method provide herein selectively binds and inhibits an exogenously administered factor Xa inhibitor in a subject undergoing anticoagulant therapy with a factor Xa inhibitor comprising administering a solution of the lyophilized formulation to the subject. The subject may be a cell or a mammal, such as a human.

Subjects that will benefit from the administration of the dissolved lyophilized formulation described herein and the accompanying methods include those that are experiencing, or predisposed to a clinical major bleeding event or a clinically significant non-major bleeding event. Examples of clinical major bleeding events are selected from the group consisting of hemorrhage, bleeding into vital organs, bleeding requiring re-operation or a new therapeutic procedure, and a bleeding index of >2.0 with an associated overt bleed. (Turpie AGG, et al, *NEJM,* 2001, 344: 619-625.) Additionally, the subject may be experiencing or predisposed to a non-major bleeding event selected from the group consisting of epistaxis that is persistent or recurrent and in substantial amount or will not stop without intervention, rectal or urinary tract bleeding that does not rise to a level requiring a therapeutic procedure, substantial hematomas at injection sites or elsewhere that are spontaneous or occur with trivial trauma, substantial blood loss more than usually associated with a surgical procedure that does not require drainage, and bleeding requiring unplanned transfusion.

In some embodiments, the dissolved lyophilized formulation is administered after the administration of an overdose of a fXa inhibitor or prior to a surgery, which may expose subjects to the risk of hemorrhage.

In any of the methods described herein, it should be understood, even if not always explicitly stated, that an effective amount of the dissolved lyophilized formulation is administered to the subject. The amount can be empirically determined by the treating physician and will vary with the age, gender, weight and health of the subject. Additional factors to be considered by the treating physician include but are not limited to the identity and/or amount of factor Xa inhibitor, which may have been administered, the method or mode that the lyophilized formulation will be administered to the subject, and the therapeutic end point for the patient. With these variables in mind, one of skill will administer a therapeutically effective amount to the subject to be treated.

EXAMPLES

The disclosure is further understood by reference to the following examples, which are intended to be purely exemplary of the disclosure. The present disclosure is not limited in scope by the exemplified embodiments, which are intended as illustrations of single aspects of the disclosure only. Any methods that are functionally equivalent are within the scope of the disclosure. Various modifications of the disclosure in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings:

hr=hour
M=molar
mg=milligram
mg/kg=milligram/kilogram
mg/mL=milligram/milliliter
min=minute
mL=milliliter
mM=millimolar
PS80=Polysorbate 80
RH=Relative humidity
w/v=Weight/volume
μL or uL=microliter
μM=Micromolar

Example 1. Preparation of Aqueous Solutions for Preparing Amorphous Formulations r-Antidote r-Antidote was manufactured in a 10 mM tris, 45 mM L-arginine HCl, 6% w/v sucrose, pH 7.8 formulation by ultrafiltration/diafiltration. r-Antidote was buffer exchanged into 10 mM tris, 45 mM L-arginine HCl, 6% w/v sucrose, pH 7.8 at 12 mg/mL, and then concentrated to 30 mg/mL. After dilution, the target r-Antidote concentration was 20 mg/mL.

Example 2a. Thermal Characterization

Eleven different formulations were prepared to test the effects of pH, mannitol (crystalline component), sucrose (stabilizer), and r-Antidote concentration on the Tg' (glass transition temperature) of the formulation. The Tg' was measured by differential scanning calorimetry (DSC). The amount of each component and Tg' of these formulations are summarized in Table 5.

Based on the above thermal characterization, it was found that formulations containing r-Antidote, Tris, L-arginine hydrochloride, mannitol, sucrose, and polysorbate 80 wherein the ratio of sucrose to mannitol were greater than 1 were amorphous and exhibited a Tg'. In formulations, such as Formulation 10a in Table 5, where the ratio of sucrose to mannitol was less than 1, a crystallization event was observed. Statistical analysis indicates that increasing amounts of sucrose and r-Antidote increase the Tg', while increasing amounts of mannitol decrease the Tg' for the amorphous formulations.

Example 2b. Thermal Characterization

Formulations of increasing concentrations of r-Antidote in 10 mM Tris, 100 mM L-arginine hydrochloride at pH 8.0 were evaluated by DSC. All formulations with a Tg' were amorphous. As shown in Table 6 below, as the protein concentration increases, the Tg' increases. Formulations with high Tg' are desirable, since they are more amenable for lyophilization, if needed.

TABLE 6

| r-Antidote Concentration (mg/mL) | Tg' (° C.) |
| --- | --- |
| 25.2 | −33.5 |
| 46.8 | −30.7 |
| 72.1 | −28.7 |
| 91.2 | −26.2 |
| 116.2 | −25.5 |

Example 3. Stability of Formulations-Liquid

The liquid formulations in Table 5 were put on stability. The formulations were tested by size exclusion chromatography (SEC) after 14 days at 5° C. and 25° C./60% RH and after 4 days at 40° C./75% RH. Ion exchange (IEX) chromatography was also performed after 4 days at 25° C./60% RH and 40° C./75% RH. Formation of SEC high molecular weight (HMW) species was primarily affected by pH, but

TABLE 5

| Formulation # | r-Antidote Concentration (mg/mL) | Tris (mM) | L-Arg HCl (mM) | Mannitol (% w/v) | Sucrose (% w/v) | PS80 (% w/v) | pH | Sucrose: r-Antidote Molar Ratio | Tg' |
| --- | --- | --- | --- | --- | --- | --- | --- | --- | --- |
| 1a | 20 | 10 | 45 | 0 | 6 | 0.01 | 7.7 | 359 | −29.7 |
| 2a | 20 | 10 | 100 | 4 | 4 | 0.01 | 6.8 | 240 | −36.0 |
| 3a | 20 | 10 | 45 | 4 | 4 | 0.01 | 7.7 | 240 | −35.9 |
| 4a | 20 | 10 | 100 | 0 | 6 | 0.01 | 6.9 | 359 | −30.1 |
| 5a | 20 | 10 | 45 | 0 | 4 | 0.01 | 6.9 | 240 | −31.6 |
| 6a | 20 | 10 | 45 | 4 | 6 | 0.01 | 6.9 | 359 | −34.7 |
| 7a | 20 | 10 | 100 | 4 | 6 | 0.01 | 7.6 | 359 | −34.3 |
| 8a | 20 | 10 | 100 | 0 | 4 | 0.01 | 7.7 | 240 | −30.9 |
| 9a | 20 | 10 | 72.5 | 2 | 5 | 0.01 | 7.3 | 299 | −34.2 |
| 10a | 11 | 10 | 45 | 5 | 2 | 0.01 | 7.6 | 240 | * |
| 11a | 39 | 10 | 100 | 0 | 6 | 0.01 | 7.6 | 180 | −27.9 |

*No Tg' detected. Solution exhibited crystallization event.

overall, all formulations retained high SEC monomer content. For IEX, there was no change after 4 days at 25° C./60% RH and an increase in acidic species with a decrease in basic species after 4 days at 40° C./75% RH. Overall, the formulations were stable as shown by SEC and IEX (Table 7).

TABLE 7

| Formulation # | Time (days) | Temperature (° C.) | SEC HMW (%) | SEC Monomer (%) | IEX % Acidic Peaks | IEX % Peak 1 | IEX % Peak 2 | IEX % Peak 3 | IEX % Basic Peaks |
|---|---|---|---|---|---|---|---|---|---|
| 1a | 0 | 5 | 1.1 | 98.8 | NT | NT | NT | NT | NT |
| 1a | 14 | 5 | 1.9 | 98.0 | NT | NT | NT | NT | NT |
| 2a | 0 | 5 | 0.6 | 99.3 | NT | NT | NT | NT | NT |
| 2a | 14 | 5 | 0.8 | 99.1 | NT | NT | NT | NT | NT |
| 3a | 0 | 5 | 1.1 | 98.8 | NT | NT | NT | NT | NT |
| 3a | 14 | 5 | 1.7 | 98.2 | NT | NT | NT | NT | NT |
| 4a | 0 | 5 | 0.7 | 99.2 | NT | NT | NT | NT | NT |
| 4a | 14 | 5 | 0.9 | 98.9 | NT | NT | NT | NT | NT |
| 5a | 0 | 5 | 0.8 | 99.1 | NT | NT | NT | NT | NT |
| 5a | 14 | 5 | 0.9 | 99.0 | NT | NT | NT | NT | NT |
| 6a | 0 | 5 | 0.9 | 99.0 | NT | NT | NT | NT | NT |
| 6a | 14 | 5 | 0.9 | 99.0 | NT | NT | NT | NT | NT |
| 7a | 0 | 5 | 1.0 | 98.9 | NT | NT | NT | NT | NT |
| 7a | 14 | 5 | 1.5 | 98.3 | NT | NT | NT | NT | NT |
| 8a | 0 | 5 | 1.0 | 99.0 | NT | NT | NT | NT | NT |
| 8a | 14 | 5 | 1.6 | 98.3 | NT | NT | NT | NT | NT |
| 9a | 0 | 5 | 0.9 | 99.0 | NT | NT | NT | NT | NT |
| 9a | 14 | 5 | 1.3 | 98.6 | NT | NT | NT | NT | NT |
| 10a | 0 | 5 | 1.0 | 99.0 | NT | NT | NT | NT | NT |
| 10a | 14 | 5 | 1.4 | 98.5 | NT | NT | NT | NT | NT |
| 11a | 0 | 5 | 1.1 | 98.8 | NT | NT | NT | NT | NT |
| 11a | 14 | 5 | 1.8 | 98.1 | NT | NT | NT | NT | NT |
| 1a | 0 | 25 | 0.7 | 99.2 | 29.7 | 20.5 | 20.2 | 8.9 | 20.6 |
| 1a | 4 | 25 | 1.3 | 98.1 | 30.9 | 20.0 | 18.6 | 9.4 | 21.0 |
| 1a | 7 | 25 | 1.2 | 98.1 | NT | NT | NT | NT | NT |
| 1a | 14 | 25 | 3.0 | 96.5 | NT | NT | NT | NT | NT |
| 2a | 0 | 25 | 0.7 | 99.2 | 29.8 | 20.8 | 20.3 | 8.7 | 20.4 |
| 2a | 4 | 25 | 1.2 | 98.4 | 30.5 | 20.0 | 18.8 | 9.4 | 21.2 |
| 2a | 7 | 25 | 1.2 | 98.2 | NT | NT | NT | NT | NT |
| 2a | 14 | 25 | 2.9 | 96.0 | NT | NT | NT | NT | NT |
| 3a | 0 | 25 | 1.2 | 98.7 | 30.1 | 20.6 | 20.1 | 8.8 | 20.4 |
| 3a | 4 | 25 | 2.3 | 97.6 | 30.9 | 20.0 | 18.3 | 9.1 | 21.7 |
| 3a | 7 | 25 | 2.5 | 97.2 | NT | NT | NT | NT | NT |
| 3a | 14 | 25 | 2.8 | 96.8 | NT | NT | NT | NT | NT |
| 4a | 0 | 25 | 0.7 | 99.2 | 29.8 | 20.7 | 20.3 | 8.8 | 20.4 |
| 4a | 4 | 25 | 1.5 | 98.0 | 29.4 | 19.7 | 19.4 | 9.8 | 21.7 |
| 4a | 7 | 25 | 1.5 | 97.8 | NT | NT | NT | NT | NT |
| 4a | 14 | 25 | 1.2 | 97.7 | NT | NT | NT | NT | NT |
| 5a | 0 | 25 | 0.8 | 99.1 | 29.6 | 21.4 | 18.6 | 8.7 | 21.7 |
| 5a | 4 | 25 | 1.1 | 98.6 | 28.5 | 20.3 | 19.2 | 10.2 | 21.8 |
| 5a | 7 | 25 | 0.9 | 98.5 | NT | NT | NT | NT | NT |
| 5a | 14 | 25 | 3.1 | 95.5 | NT | NT | NT | NT | NT |
| 6a | 0 | 25 | 0.9 | 99.1 | 29.6 | 21.2 | 20.5 | 8.7 | 19.9 |
| 6a | 4 | 25 | 1.2 | 98.5 | 30.8 | 19.8 | 18.6 | 9.3 | 21.4 |
| 6a | 7 | 25 | 1.0 | 98.5 | NT | NT | NT | NT | NT |
| 6a | 14 | 25 | 2.3 | 96.4 | NT | NT | NT | NT | NT |
| 7a | 0 | 25 | 1.1 | 98.8 | 30.5 | 20.3 | 20.4 | 9.1 | 19.6 |
| 7a | 4 | 25 | 2.2 | 97.5 | 30.4 | 19.3 | 18.9 | 9.4 | 22.1 |
| 7a | 7 | 25 | 2.4 | 97.1 | NT | NT | NT | NT | NT |
| 7a | 14 | 25 | 2.7 | 96.6 | NT | NT | NT | NT | NT |
| 8a | 0 | 25 | 1.0 | 98.9 | 29.7 | 20.3 | 20.0 | 8.8 | 21.2 |
| 8a | 4 | 25 | 2.4 | 97.5 | 31.6 | 19.8 | 18.9 | 9.5 | 20.2 |
| 8a | 7 | 25 | 2.7 | 96.9 | NT | NT | NT | NT | NT |
| 8a | 14 | 25 | 3.3 | 96.4 | NT | NT | NT | NT | NT |
| 9a | 0 | 25 | 1.0 | 99.0 | 30.1 | 20.2 | 20.0 | 8.8 | 20.9 |
| 9a | 4 | 25 | 2.2 | 97.4 | 30.8 | 19.6 | 19.3 | 9.7 | 20.6 |
| 9a | 7 | 25 | 2.4 | 97.2 | NT | NT | NT | NT | NT |
| 9a | 14 | 25 | 2.7 | 96.8 | NT | NT | NT | NT | NT |
| 10a | 0 | 25 | 1.0 | 98.9 | 31.4 | 18.8 | 20.6 | 8.9 | 20.3 |
| 10a | 4 | 25 | 1.9 | 97.8 | 29.9 | 18.8 | 18.7 | 9.3 | 23.3 |
| 10a | 7 | 25 | 2.1 | 97.6 | NT | NT | NT | NT | NT |
| 10a | 14 | 25 | 2.3 | 97.3 | NT | NT | NT | NT | NT |
| 11a | 0 | 25 | 1.1 | 98.8 | 30.4 | 20.1 | 21.0 | 9.8 | 18.7 |
| 11a | 4 | 25 | 2.8 | 97.0 | 31.7 | 19.4 | 19.0 | 9.7 | 20.2 |
| 11a | 7 | 25 | 3.2 | 96.5 | NT | NT | NT | NT | NT |
| 11a | 14 | 25 | 4.2 | 95.4 | NT | NT | NT | NT | NT |
| 1a | 0 | 40 | 0.7 | 99.2 | 29.7 | 20.5 | 20.2 | 8.9 | 20.6 |
| 1a | 4 | 40 | 5.9 | 93.1 | 42.3 | 20.8 | 16.6 | 8.4 | 11.9 |
| 2a | 0 | 40 | 0.7 | 99.2 | 29.8 | 20.8 | 20.3 | 8.7 | 20.4 |
| 2a | 4 | 40 | 5.9 | 93.1 | 30.5 | 18.0 | 18.6 | 11.2 | 21.7 |
| 3a | 0 | 40 | 1.2 | 98.7 | 30.1 | 20.6 | 20.1 | 8.8 | 20.4 |

TABLE 7-continued

| Formulation # | Time (days) | Temperature (° C.) | SEC HMW (%) | SEC Monomer (%) | IEX % Acidic Peaks | IEX % Peak 1 | IEX % Peak 2 | IEX % Peak 3 | IEX % Basic Peaks |
|---|---|---|---|---|---|---|---|---|---|
| 3a | 4 | 40 | 12.1 | 87.7 | 40.7 | 20.9 | 16.4 | 8.0 | 14.0 |
| 4a | 0 | 40 | 0.7 | 99.2 | 29.8 | 20.7 | 20.3 | 8.8 | 20.4 |
| 4a | 4 | 40 | 7.8 | 91.6 | 34.2 | 19.1 | 18.0 | 10.0 | 18.7 |
| 5a | 0 | 40 | 0.8 | 99.1 | 29.6 | 21.4 | 18.6 | 8.7 | 21.7 |
| 5a | 4 | 40 | 9.0 | 90.3 | 33.7 | 19.1 | 18.0 | 10.5 | 18.7 |
| 6a | 0 | 40 | 0.9 | 99.1 | 29.6 | 21.2 | 20.5 | 8.7 | 19.9 |
| 6a | 4 | 40 | 5.1 | 94.0 | 31.0 | 18.2 | 18.5 | 10.8 | 21.5 |
| 7a | 0 | 40 | 1.1 | 98.8 | 30.5 | 20.3 | 20.4 | 9.1 | 19.6 |
| 7a | 4 | 40 | 8.9 | 91.0 | 40.0 | 20.5 | 16.1 | 8.0 | 15.4 |
| 8a | 0 | 40 | 1.0 | 98.9 | 29.7 | 20.3 | 20.0 | 8.8 | 21.2 |
| 8a | 4 | 40 | 12.7 | 87.0 | 41.9 | 20.4 | 16.4 | 7.9 | 13.4 |
| 9a | 0 | 40 | 1.0 | 99.0 | 30.1 | 20.2 | 20.0 | 8.8 | 20.9 |
| 9a | 4 | 40 | 8.2 | 91.6 | 36.7 | 20.0 | 17.1 | 9.0 | 17.1 |
| 10a | 0 | 40 | 1.0 | 98.9 | 31.4 | 18.8 | 20.6 | 8.9 | 20.3 |
| 10a | 4 | 40 | 5.8 | 94.0 | 37.3 | 20.8 | 17.4 | 12.8 | 11.6 |
| 11a | 0 | 40 | 1.1 | 98.8 | 30.4 | 20.1 | 21.0 | 9.8 | 18.7 |
| 11a | 4 | 40 | 19.3 | 80.4 | 41.8 | 20.6 | 16.5 | 8.3 | 12.8 |

NT = not tested

Example 4. Collapse Temperature

Two formulations were evaluated by freeze dry microscopy to identify their collapse temperature.

Approximately 0.15 mL of solution was dispensed into a glass cell. The cell was placed on a temperature-controlled freeze-drying stage. The sample cell had 2 thermocouples placed directly into the material at the bottom and center of the cell. The liquid samples was cooled at 0.5° C./min to −60° C. The stage chamber was evacuated to initiate sublimation. The stage was then warmed at an average rate of 0.5° C./min. The sample was examined for collapse using an Infinivar Microscope capable of magnification from 16 to 330× coupled to a Super WDR CCD Camera.

A formulation of 20 mg/mL r-Antidote, 10 mM tris, 45 mM L-arginine, 6% w/v sucrose, 0.01% w/v polysorbate 80 at pH 7.8, exhibited a collapse temperature of −26° C.

A formulation of 40 mg/mL r-Antidote, 10 mM tris, 45 mM L-arginine, 6% w/v sucrose, 0.01% w/v polysorbate 80 at pH 7.8 exhibited a collapse temperature of −24° C.

The collapse temperature of the two formulations are sufficiently high enough for the development of a lyophilization cycle.

Example 5. Lyophilization

The formulations summarized in Table 8 were lyophilized using the lyophilization cycle summarized in Table 9. 2.5 mL of each formulation was filled into 5 mL glass vials and partially stoppered prior to start of the lyophilization cycle.

TABLE 8

| Formulation # | r-Antidote (mg/mL) | Tris (mM) | Arginine (mM) | Sucrose (mM) | Mannitol (mM) | PS80 (%) | pH | Sucrose:r-Antidote Molar Ratio |
|---|---|---|---|---|---|---|---|---|
| 1b | 20 | 10 | 45 | 6 | 0 | 0.01 | 7.8 | 359 |
| 2b | 40 | 10 | 100 | 6 | 0 | 0.01 | 7.8 | 180 |
| 3b | 20 | 10 | 45 | 2 | 5 | 0.01 | 7.8 | 120 |

TABLE 9

| Step Description | Process Parameter | Target |
|---|---|---|
| Freezing | Freezing Ramp Rate (° C./min) | 1 |
| | Freezing Shelf Temperature (° C.) | −40 |
| | Freezing Hold Time (min) | >180 |
| Annealing | Annealing Ramp Rate (° C./min) | 1 |
| | Annealing Hold Shelf Temperature (° C.) | −20 |
| | Annealing Hold Time (min) | >180 |
| Refreezing | Refreezing Ramp Rate (° C./min) | 1 |
| | Refreezing Shelf Temperature (° C.) | −40 |
| | Refreezing Hold Time (min) | >180 |
| Primary Drying | Ramp Rate (° C./min) | 0.5 |
| | Shelf Temperature (° C.) | −30.0 |
| | Chamber Pressure (mTorr) | 100 |
| | Hold Time (min) | Hold until Pirani indicates completion |
| Secondary Drying | Ramp Rate (° C./min) | 0.5 |
| | Shelf Temperature (° C.) | 25 |
| | Chamber Pressure (mTorr) | 75 |

TABLE 9-continued

| Step Description | Process Parameter | Target |
|---|---|---|
| | Hold Time (min) | Hold until pirani indicates completion (4-8 hours) |
| Stoppering | Backfill Pressure (manual stoppering) | Atmosphere |
| | Temperature | 5 C. |
| | Ramp Rate | 1 C. |

All lyophilized formulations were solid in appearance and pharmaceutically elegant. Formulation 1b exhibited minor collapse, while Formulations 2b and 3b did not show any collapse.

Example 6. Stability of Lyophilized Formulations

The lyophilized formulations were placed on accelerated stability at 40° C./75% RH for up to 1 month. The stability results as determined by SEC, HPLC, and IEX are shown below in Tables 10, 11, and 12, respectively. The formulations are stable up to 1 month at 40° C.

TABLE 10

| Formulation # | Time (weeks) | Protein Concentration (mg/mL) | Moisture (% w/w) | SEC % HMW | SEC % Monomer | SEC % Post-Peak |
|---|---|---|---|---|---|---|
| 1b | 0 | 26.0 | 0.7 | 1.4 | 98.6 | 0.0 |
| 1b | 2 | 25.9 | — | 1.6 | 98.3 | 0.1 |
| 1b | 4 | 25.9 | — | 1.5 | 98.5 | 0.1 |
| 2b | 0 | 46.5 | 0.5 | 1.3 | 98.6 | 0.1 |
| 2b | 2 | 44.4 | — | 1.6 | 98.4 | 0.1 |
| 2b | 4 | 45.6 | — | 1.4 | 98.5 | 0.1 |
| 3b | 0 | 17.6 | 0.6 | 0.8 | 99.2 | 0.1 |
| 3b | 2 | 17.2 | — | 1.1 | 98.9 | 0.0 |
| 3b | 4 | 17.3 | — | 1.0 | 98.9 | 0.1 |

TABLE 11

| Formulation # | Time (weeks) | Protein Concentration (mg/mL) | Moisture (% w/w) | RP-HPLC % Pre-Peaks | RP-HPLC % Main Peak | RP-HPLC % BetaPeak | RP-HPLC % Post Peaks |
|---|---|---|---|---|---|---|---|
| 1b | 0 | 26.0 | 0.7 | 0.7 | 89.9 | 9.2 | 0.3 |
| 1b | 2 | 25.9 | — | 0.9 | 88.6 | 9.1 | 1.4 |
| 1b | 4 | 25.9 | — | 1.0 | 89.0 | 9.0 | 1.1 |
| 2b | 0 | 46.5 | 0.5 | 0.7 | 89.8 | 9.2 | 0.4 |
| 2b | 2 | 44.4 | — | 1.0 | 89.2 | 8.4 | 1.4 |
| 2b | 4 | 45.6 | — | 1.0 | 88.9 | 8.9 | 1.1 |
| 3b | 0 | 17.6 | 0.6 | 0.5 | 91.8 | 7.4 | 0.3 |
| 3b | 2 | 17.2 | — | 0.7 | 90.9 | 7.3 | 1.1 |
| 3b | 4 | 17.3 | — | 1.1 | 90.6 | 7.1 | 1.3 |

TABLE 12

| Formulation # | Time (weeks) | Protein Concentration (mg/mL) | Moisture (% w/w) | IEX % Acidic Peaks | IEX % Peak 1 | IEX % Peak 2 | IEX % Peak 3 | IEX % Basic Peaks |
|---|---|---|---|---|---|---|---|---|
| 1b | 0 | 26.0 | 0.7 | 31.3 | 17.6 | 20.3 | 8.6 | 22.2 |
| 1b | 2 | 25.9 | — | 30.0 | 15.8 | 18.3 | 8.1 | 27.7 |
| 1b | 4 | 25.9 | — | 33.5 | 21.5 | 17.1 | 7.4 | 20.5 |
| 2b | 0 | 46.5 | 0.5 | 31.5 | 17.1 | 20.8 | 8.8 | 21.8 |
| 2b | 2 | 44.4 | — | 29.8 | 14.8 | 17.7 | 7.9 | 29.9 |
| 2b | 4 | 45.6 | — | 33.2 | 21.0 | 17.4 | 7.9 | 20.6 |
| 3b | 0 | 17.6 | 0.6 | 31.8 | 16.9 | 20.5 | 8.8 | 21.9 |
| 3b | 2 | 17.2 | — | 29.8 | 14.7 | 17.4 | 7.9 | 30.2 |
| 3b | 4 | 17.3 | — | 33.2 | 21.0 | 17.9 | 7.3 | 20.5 |

Example 7. r-Antidote Solubility

The solubility of r-Antidote in various pH and various concentrations of excipients was examined. r-Antidote was buffer exchanged and concentrated into the formulations detailed in Table 13. The solutions were filtered with a 0.45 µm filter. Visual appearance, concentration, and pH measurements were performed for the formulations at room temperature. The protein increases in solubility with increasing pH from 6.8 to 7.8. For formulations containing L-Arginine hydrochloride from 25 mM to 100 mM, the concentrations obtained ranged from 114 to 151 mg/mL. The solutions were clear, indicating that the protein could be concentrated higher, and the solubility limit was not reached. With the addition of L-arginine hydrochloride, the effects of pH are lessened on solubility. Based on these results, formulations of high concentrations of r-Antidote can be achieved at higher pHs or with the addition of L-arginine hydrochloride. Based on Example 2b, higher protein concentration formulations decrease the Tg', which allow for more efficient lyophilization cycles for the manufacturing of lyophilized protein solutions.

TABLE 13

| Sample | Tris Conc. (mM) | L-Arginine Hydrochloride Conc. (mM) | Sucrose Conc. (% w/v) | Visual Appearance Prior to Filtration | Measured pH | Protein Conc. (mg/mL) |
|---|---|---|---|---|---|---|
| 1 | 10 | 0 | 0 | Cloudy | 6.8 | 11.4 |
| 2 | 10 | 0 | 0 | Cloudy | 7.1 | 30.4 |
| 3 | 10 | 0 | 0 | Cloudy | 7.5 | 54.0 |
| 4 | 10 | 0 | 0 | Cloudy | 7.8 | 94.6 |
| 5 | 10 | 100 | 0 | Clear* | 6.7 | 126.2 |
| 6 | 10 | 100 | 0 | Clear* | 8.0 | 137.5 |
| 7 | 10 | 100 | 6 | Clear* | 8.0 | 114.2 |
| 8 | 10 | 45 | 4 | Clear* | 7.7 | 130.5 |
| 9 | 10 | 25 | 0 | Clear* | 8.0 | 129.6 |
| 10 | 10 | 50 | 0 | Clear* | 8.0 | 151.3 |
| 11 | 10 | 75 | 0 | Clear* | 8.1 | 137.9 |

*Conc. = concentration. Formulations were clear indicating the solubility limit was not reached. Concentration values reported are values obtained from concentrating the solution but are not representative of the solubility limit

The invention claimed is:

1. A lyophilized composition prepared by lyophilizing an aqueous formulation, wherein: the aqueous formulation comprises a stabilizer, from 25 mM to 110 mM arginine, and a two-chain polypeptide comprising a first chain comprising the amino acid sequence of SEQ ID NO. 4, and a second chain comprising the amino acid sequence of SEQ ID NO. 5, wherein the polypeptide cannot assemble into a prothrombinase complex; the aqueous formulation has a pH from 7.7 to 7.9; the stabilizer comprises from 5.5% to 7.5% sucrose (w/v); and the molar ratio of the stabilizer to the polypeptide is at least 100, and wherein the aqueous formulation does not include mannitol.

2. The composition of claim 1, wherein the aqueous formulation comprises from 40 mM to 50 mM arginine and 20 mg/mL of the polypeptide.

3. The composition of claim 1, wherein the aqueous formulation comprises from 90 mM to 110 mM arginine at least 30 mg/mL of the polypeptide.

4. The composition of claim 3, wherein the aqueous formulation comprises 45 mg/mL of the polypeptide.

5. The composition of claim 1, wherein the aqueous formulation comprises 40 mg/mL of the polypeptide.

6. The composition of claim 1, wherein the polypeptide comprises an amino acid residue that is modified to be different from natural amino acids.

7. The composition of claim 1, wherein the first chain comprises the amino acid sequence of SEQ ID NO. 2, and the second chain comprises the amino acid sequence of SEQ ID NO. 3.

8. The composition of claim 7, wherein residue Asp29 of the first chain is modified to (3R)-3-hydroxyAsp.

9. The composition of claim 1, wherein the polypeptide comprises at least an intra-chain disulfide bond for each of the first and second chains.

10. A lyophilized composition prepared by lyophilizing an aqueous formulation, wherein: the aqueous formulation comprises about 45 mM arginine, about 6% sucrose (w/v), 0% mannitol, and a two-chain polypeptide comprising a first chain comprising the amino acid sequence of SEQ ID NO. 4, and a second chain comprising the amino acid sequence of SEQ ID NO. 5, wherein the polypeptide cannot assemble into a prothrombinase complex; and the aqueous formulation has a pH of about 7.8.

11. A lyophilized composition prepared by lyophilizing an aqueous formulation, wherein: the aqueous formulation comprises about 100 mM arginine, about 6% sucrose (w/v), 0% mannitol, and a two-chain polypeptide comprising a first chain comprising the amino acid sequence of SEQ ID NO. 4, and a second chain comprising the amino acid sequence of SEQ ID NO. 5, wherein the polypeptide cannot assemble into a prothrombinase complex; and the aqueous formulation has a pH of about 7.8.

12. The composition of claim 11, wherein the two-chain polypeptide has modifications to the Gla domain and the active site as compared to the wild-type fXa protein, is able to bind to a fXa inhibitor but does not assemble into a prothrombinase complex.

13. The composition of claim 1, which has a glass transition temperature from about −27° C. to about −37° C.

14. The composition of claim 1, wherein the aqueous formulation further comprises a surfactant and a buffer.

15. A method of preparing the lyophilized composition of claim 1, comprising lyophilizing an aqueous formulation, wherein:
the aqueous formulation comprises a stabilizer, from 25 mM to 110 mM arginine, and the polypeptide;
the aqueous formulation has a pH from 7.7 to 7.9;
the stabilizer comprises from 5.5% to 7.5% sucrose (w/v); and the molar ratio of the stabilizer to the polypeptide is at least 100, and wherein the aqueous formulation does not include mannitol.

16. A method of reducing bleeding in a subject undergoing anticoagulant therapy with a factor Xa inhibitor comprising administering to the subject a solution prepared by dissolving the composition of claim 1 in an aqueous solvent.

17. The method of claim 16, wherein the factor Xa inhibitor is apixaban, rivaroxaban or betrixaban.

18. The composition of claim 1, which comprises at least 15 mg/mL of the polypeptide.

* * * * *

SEQUENCE LISTING

<160> NUMBER OF SEQ ID NOS: 9

<210> SEQ ID NO 1
<211> LENGTH: 448
<212> TYPE: PRT
<213> ORGANISM: Homo sapiens

<400> SEQUENCE: 1

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
            85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
```

-continued

```
                        165                 170                 175
Leu Leu Asp Phe Asn Gln Thr Gln Pro Glu Arg Gly Asp Asn Asn Leu
                180                 185                 190

Thr Arg Ile Val Gly Gly Gln Glu Cys Lys Asp Gly Glu Cys Pro Trp
            195                 200                 205

Gln Ala Leu Leu Ile Asn Glu Glu Asn Glu Gly Phe Cys Gly Gly Thr
        210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
        435                 440                 445
```

<210> SEQ ID NO 2
<211> LENGTH: 105
<212> TYPE: PRT
<213> ORGANISM: Homo sapiens

<400> SEQUENCE: 2

```
Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
                20                  25                  30

Glu Tyr Thr Cys Thr Cys Leu Glu Gly Phe Glu Gly Lys Asn Cys Glu
            35                  40                  45

Leu Phe Thr Arg Lys Leu Cys Ser Leu Asp Asn Gly Asp Cys Asp Gln
        50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95
```

Pro Cys Gly Lys Gln Thr Leu Glu Arg
            100                 105

<210> SEQ ID NO 3
<211> LENGTH: 254
<212> TYPE: PRT
<213> ORGANISM: Homo sapiens

<400> SEQUENCE: 3

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 4
<211> LENGTH: 11
<212> TYPE: PRT
<213> ORGANISM: Homo sapiens

<400> SEQUENCE: 4

Pro Tyr Pro Cys Gly Lys Gln Thr Leu Glu Arg
1               5                   10

<210> SEQ ID NO 5
<211> LENGTH: 234
<212> TYPE: PRT
<213> ORGANISM: Homo sapiens

<400> SEQUENCE: 5

Ile Val Gly Gly Gln Glu Cys Lys Asp Gly Glu Cys Pro Trp Gln Ala

```
            1               5                   10                  15
          Leu Leu Ile Asn Glu Glu Asn Glu Gly Phe Cys Gly Gly Thr Ile Leu
                          20                  25                  30

Ser Glu Phe Tyr Ile Leu Thr Ala Ala His Cys Leu Tyr Gln Ala Lys
                          35                  40                  45

Arg Phe Lys Val Arg Val Gly Asp Arg Asn Thr Glu Gln Glu Glu Gly
                          50                  55                  60

Gly Glu Ala Val His Glu Val Glu Val Val Ile Lys His Asn Arg Phe
          65                      70                  75                  80

Thr Lys Glu Thr Tyr Asp Phe Asp Ile Ala Val Leu Arg Leu Lys Thr
                          85                  90                  95

Pro Ile Thr Phe Arg Met Asn Val Ala Pro Ala Cys Leu Pro Glu Arg
                          100                 105                 110

Asp Trp Ala Glu Ser Thr Leu Met Thr Gln Lys Thr Gly Ile Val Ser
                          115                 120                 125

Gly Phe Gly Arg Thr His Glu Lys Gly Arg Gln Ser Thr Arg Leu Lys
                          130                 135                 140

Met Leu Glu Val Pro Tyr Val Asp Arg Asn Ser Cys Lys Leu Ser Ser
          145                     150                 155                 160

Ser Phe Ile Ile Thr Gln Asn Met Phe Cys Ala Gly Tyr Asp Thr Lys
                          165                 170                 175

Gln Glu Asp Ala Cys Gln Gly Asp Ala Gly Gly Pro His Val Thr Arg
                          180                 185                 190

Phe Lys Asp Thr Tyr Phe Val Thr Gly Ile Val Ser Trp Gly Glu Gly
                          195                 200                 205

Cys Ala Arg Lys Gly Lys Tyr Gly Ile Tyr Thr Lys Val Thr Ala Phe
                          210                 215                 220

Leu Lys Trp Ile Asp Arg Ser Met Lys Thr
          225                     230

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Lys Arg Arg Lys Arg
1               5

<210> SEQ ID NO 7
<211> LENGTH: 346
<212> TYPE: PRT
<213> ORGANISM: Homo sapiens

<400> SEQUENCE: 7

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
                20                  25                  30

Glu Tyr Thr Cys Thr Cys Leu Glu Gly Phe Glu Gly Lys Asn Cys Glu
                35                  40                  45

Leu Phe Thr Arg Lys Leu Cys Ser Leu Asp Asn Gly Asp Cys Asp Gln
                50                  55                  60

Phe Cys His Glu Glu Gln Asn Ser Val Val Cys Ser Cys Ala Arg Gly
```

```
              65                  70                  75                  80
        Tyr Thr Leu Ala Asp Asn Arg Lys Arg Lys Arg Ile Val Gly Gly
                            85                  90                  95

Gln Glu Cys Lys Asp Gly Glu Cys Pro Trp Gln Ala Leu Leu Ile Asn
                        100                 105                 110

Glu Glu Asn Glu Gly Phe Cys Gly Gly Thr Ile Leu Ser Glu Phe Tyr
                        115                 120                 125

Ile Leu Thr Ala Ala His Cys Leu Tyr Gln Ala Lys Arg Phe Lys Val
                    130                 135                 140

Arg Val Gly Asp Arg Asn Thr Glu Gln Glu Glu Gly Gly Glu Ala Val
        145                 150                 155                 160

His Glu Val Glu Val Val Ile Lys His Asn Arg Phe Thr Lys Glu Thr
                            165                 170                 175

Tyr Asp Phe Asp Ile Ala Val Leu Arg Leu Lys Thr Pro Ile Thr Phe
                        180                 185                 190

Arg Met Asn Val Ala Pro Ala Cys Leu Pro Glu Arg Asp Trp Ala Glu
                        195                 200                 205

Ser Thr Leu Met Thr Gln Lys Thr Gly Ile Val Ser Gly Phe Gly Arg
                    210                 215                 220

Thr His Glu Lys Gly Arg Gln Ser Thr Arg Leu Lys Met Leu Glu Val
        225                 230                 235                 240

Pro Tyr Val Asp Arg Asn Ser Cys Lys Leu Ser Ser Phe Ile Ile
                            245                 250                 255

Thr Gln Asn Met Phe Cys Ala Gly Tyr Asp Thr Lys Gln Glu Asp Ala
                        260                 265                 270

Cys Gln Gly Asp Ala Gly Gly Pro His Val Thr Arg Phe Lys Asp Thr
                    275                 280                 285

Tyr Phe Val Thr Gly Ile Val Ser Trp Gly Glu Gly Cys Ala Arg Lys
                    290                 295                 300

Gly Lys Tyr Gly Ile Tyr Thr Lys Val Thr Ala Phe Leu Lys Trp Ile
        305                 310                 315                 320

Asp Arg Ser Met Lys Thr Arg Gly Leu Pro Lys Ala Lys Ser His Ala
                        325                 330                 335

Pro Glu Val Ile Thr Ser Ser Pro Leu Lys
                        340                 345

<210> SEQ ID NO 8
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Asn Ser Phe Leu Phe Trp Asn Lys Tyr Lys Asp Gly Asp Gln Cys
        1               5                   10                  15

Glu Thr Ser Pro Cys Gln Asn Gly Lys Cys Lys Asp Gly Leu Gly
                        20                  25                  30

Glu Tyr Thr Cys Thr Cys Leu Glu Gly Phe Glu Gly Lys Asn Cys Glu
                    35                  40                  45

Leu Phe Thr Arg Lys Leu Cys Ser Leu Asp Asn Gly Asp Cys Asp Gln
                    50                  55                  60

Phe Cys His Glu Glu Gln Asn Ser Val Val Cys Ser Cys Ala Arg Gly
        65                  70                  75                  80
```

```
Tyr Thr Leu Ala Asp Asn Gly Lys Ala Cys Ile Pro Thr Gly Pro Tyr
                85                  90                  95

Pro Cys Gly Lys Gln Thr Leu Glu Arg Ile Val Gly Gly Gln Glu Cys
            100                 105                 110

Lys Asp Gly Glu Cys Pro Trp Gln Ala Leu Leu Ile Asn Glu Glu Asn
        115                 120                 125

Glu Gly Phe Cys Gly Gly Thr Ile Leu Ser Glu Phe Tyr Ile Leu Thr
    130                 135                 140

Ala Ala His Cys Leu Tyr Gln Ala Lys Arg Phe Lys Val Arg Val Gly
145                 150                 155                 160

Asp Arg Asn Thr Glu Gln Glu Glu Gly Gly Glu Ala Val His Glu Val
                165                 170                 175

Glu Val Val Ile Lys His Asn Arg Phe Thr Lys Glu Thr Tyr Asp Phe
            180                 185                 190

Asp Ile Ala Val Leu Arg Leu Lys Thr Pro Ile Thr Phe Arg Met Asn
        195                 200                 205

Val Ala Pro Ala Cys Leu Pro Glu Arg Asp Trp Ala Glu Ser Thr Leu
    210                 215                 220

Met Thr Gln Lys Thr Gly Ile Val Ser Gly Phe Gly Arg Thr His Glu
225                 230                 235                 240

Lys Gly Arg Gln Ser Thr Arg Leu Lys Met Leu Glu Val Pro Tyr Val
                245                 250                 255

Asp Arg Asn Ser Cys Lys Leu Ser Ser Ser Phe Ile Ile Thr Gln Asn
            260                 265                 270

Met Phe Cys Ala Gly Tyr Asp Thr Lys Gln Glu Asp Ala Cys Gln Gly
        275                 280                 285

Asp Ala Gly Gly Pro His Val Thr Arg Phe Lys Asp Thr Tyr Phe Val
    290                 295                 300

Thr Gly Ile Val Ser Trp Gly Glu Gly Cys Ala Arg Lys Gly Lys Tyr
305                 310                 315                 320

Gly Ile Tyr Thr Lys Val Thr Ala Phe Leu Lys Trp Ile Asp Arg Ser
                325                 330                 335

Met Lys Thr Arg Gly Leu Pro Lys Ala Lys Ser His Ala Pro Glu Val
            340                 345                 350

Ile Thr Ser Ser Pro Leu Lys
        355

<210> SEQ ID NO 9
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Tyr Pro Cys Gly Lys Gln Thr Leu Glu Arg Ile Val Gly Gly Gln
1               5                   10                  15

Glu Cys Lys Asp Gly Glu Cys Pro Trp Gln Ala Leu Leu Ile Asn Glu
            20                  25                  30

Glu Asn Glu Gly Phe Cys Gly Gly Thr Ile Leu Ser Glu Phe Tyr Ile
        35                  40                  45

Leu Thr Ala Ala His Cys Leu Tyr Gln Ala Lys Arg Phe Lys Val Arg
    50                  55                  60

Val Gly Asp Arg Asn Thr Glu Gln Glu Glu Gly Gly Glu Ala Val His
65                  70                  75                  80
```

-continued

```
Glu Val Glu Val Val Ile Lys His Asn Arg Phe Thr Lys Glu Thr Tyr
                85              His     90              95

Asp Phe Asp Ile Ala Val Leu Arg Leu Lys Thr Pro Ile Thr Phe Arg
            100             105             110

Met Asn Val Ala Pro Ala Cys Leu Pro Glu Arg Asp Trp Ala Glu Ser
        115             120             125

Thr Leu Met Thr Gln Lys Thr Gly Ile Val Ser Gly Phe Gly Arg Thr
        130             135             140

His Glu Lys Gly Arg Gln Ser Thr Arg Leu Lys Met Leu Glu Val Pro
145             150             155             160

Tyr Val Asp Arg Asn Ser Cys Lys Leu Ser Ser Ser Phe Ile Ile Thr
            165             170             175

Gln Asn Met Phe Cys Ala Gly Tyr Asp Thr Lys Gln Glu Asp Ala Cys
        180             185             190

Gln Gly Asp Ala Gly Gly Pro His Val Thr Arg Phe Lys Asp Thr Tyr
        195             200             205

Phe Val Thr Gly Ile Val Ser Trp Gly Glu Gly Cys Ala Arg Lys Gly
    210             215             220

Lys Tyr Gly Ile Tyr Thr Lys Val Thr Ala Phe Leu Lys Trp Ile Asp
225             230             235             240

Arg Ser Met Lys Thr
            245
```